United States Patent
Suzuki et al.

(10) Patent No.: US 7,939,563 B2
(45) Date of Patent: *May 10, 2011

(54) REMEDY FOR HYPERTENSION

(75) Inventors: Atsushi Suzuki, Haga-gun (JP); Ryuji Ochiai, Haga-gun (JP); Ichiro Tokimitsu, Haga-gun (JP)

(73) Assignee: Kao Corporation, Tokyo (JP)

( * ) Notice: Subject to any disclaimer, the term of this patent is extended or adjusted under 35 U.S.C. 154(b) by 90 days.

This patent is subject to a terminal disclaimer.

(21) Appl. No.: 11/106,428

(22) Filed: Apr. 15, 2005

(65) Prior Publication Data

US 2005/0215632 A1 Sep. 29, 2005

Related U.S. Application Data

(63) Continuation of application No. 10/810,611, filed on Mar. 29, 2004, now Pat. No. 7,534,815, which is a continuation of application No. 10/161,739, filed on Jun. 5, 2002, now Pat. No. 6,894,077.

(30) Foreign Application Priority Data

Jun. 5, 2001 (JP) .................................. 2001-169261

(51) Int. Cl.
*A61K 31/195* (2006.01)
*A61K 31/19* (2006.01)
*A61K 31/045* (2006.01)
*A61K 31/05* (2006.01)

(52) U.S. Cl. ........ 514/561; 514/563; 514/567; 514/568; 514/730; 514/734

(58) Field of Classification Search ...................... 514/57, 514/561, 563, 567, 568, 730, 734
See application file for complete search history.

(56) References Cited

U.S. PATENT DOCUMENTS

| | | | |
|---|---|---|---|
| 6,310,100 | B1 | 10/2001 | Suzuki et al. |
| 6,458,392 | B1 * | 10/2002 | Okawa et al. ................. 424/776 |
| 6,894,077 | B2 * | 5/2005 | Suzuki et al. ................. 514/534 |
| 6,991,812 | B2 * | 1/2006 | Suzuki et al. ................. 424/725 |
| 7,125,573 | B2 * | 10/2006 | Okawa et al. ................. 424/776 |
| 7,534,815 | B2 * | 5/2009 | Suzuki et al. ................. 514/543 |
| 2002/0012708 | A1 * | 1/2002 | Ruepp ........................... 424/725 |
| 2002/0051810 | A1 | 5/2002 | Suzuki et al. |
| 2002/0054923 | A1 | 5/2002 | Suzuki et al. |
| 2002/0192317 | A1 | 12/2002 | Okawa et al. |
| 2004/0043057 | A1 | 3/2004 | Suzuki et al. |
| 2004/0151790 | A1 | 8/2004 | Suzuki et al. |
| 2004/0192773 | A1 | 9/2004 | Suzuki et al. |
| 2004/0198807 | A1 | 10/2004 | Suzuki et al. |

FOREIGN PATENT DOCUMENTS

| | | |
|---|---|---|
| CN | 1192357 A | 9/1998 |
| EP | 0 387 000 | 9/1990 |
| EP | 1 090 635 | 4/2001 |
| EP | 1 172 112 | 1/2002 |
| EP | 1 186 294 | 3/2002 |
| EP | 1 186 297 | 3/2002 |
| FR | 2 302 745 | 10/1976 |
| FR | 2 734 478 | 11/1996 |
| JP | 61-40298 | 2/1986 |
| JP | 4-316597 | 11/1992 |
| JP | 7-285876 | 10/1995 |
| WO | WO 91/01724 | 2/1991 |
| WO | WO 92/16544 | 10/1992 |
| WO | WO 98/01143 | 1/1998 |
| WO | WO 01/12178 | 2/2001 |
| WO | WO 02/24212 | 3/2002 |

OTHER PUBLICATIONS

Cheng et al. (The Chinese Pharmaceutical Journal, 1994, 46, pp. 575-582.*

Dranik, "Spectral investigation of phenolcarboxylic acids of *Cynara scolymus*", Khimiya Prirodnykh Soedinenii, vol. 2, No. 5, pp. 303-306 (1966) abstract enclosed.*

STN, Registry File, "Neochlorogenic acid" other name known as "5-Caffeoylquinic acid" (2010).*

(Continued)

*Primary Examiner* — Kevin Weddington
(74) *Attorney, Agent, or Firm* — Oblon, Spivak, McClelland, Maier & Neustadt, L.L.P.

(57) ABSTRACT

Provided is a method of treating hypertension, which comprises administering an effective amount of a compound represented by the following formula (1) or (2):

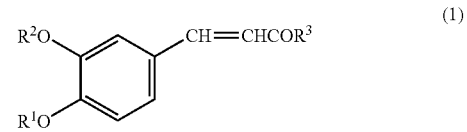

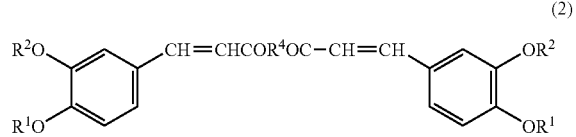

wherein, $R^1$ and $R^2$ are the same or different and each independently represents hydrogen, alkyl, alkenyl, cycloalkyl, cycloalkenyl, alkoxyalkyl, aryl, alkylaryl, aralkyl, or acyl, $R^3$ represents hydroxyl, ester bond residue, or amide bond residue, $R^4$ represents ester bond residue or amide bond residue, or a pharmaceutically acceptable salt thereof (except ferulic acid).

When the preventive or remedy for hypertension according to the present invention is administered, ferulic acid exists in the blood for a long period of time, thereby continuously suppressing a blood pressure rise. Moreover, the hypertension preventive or remedy according to the present invention has reduced in bitterness peculiar to ferulic acid, which enables patients to take it continuously.

18 Claims, No Drawings

OTHER PUBLICATIONS

Derwent Publications, AN 1992-337587, XP-002219275, JP 04-243822, Aug. 31, 1992.

J-T. Cheng, et al., Chemical Abstracts, 1 page, XP-002219274, "Antihypertensive Activity of Phenolics From the Flower of *Lonicera japonica*", 1994.

M. Carmignani, et al., Journal of Medicinal Chemistry, vol. 44, No. 18, pp. 2950-2958, XP002219273, "Novel Hypotensive Agents From *Verbesina caracasana*, 8. Synthesis and Pharmacology of (3,4-Dimethoxycinnamoyl_-$N^1$-Agmatine and Synthetic Analogues", 2001.

H.P. Pham, et al., Prostaglandins in Clinical Research, pp. 609-613, XP-008007450, "Comparative Effects on TXA2 Biosynthesis of Compounds Extracted From Three Verbenaceae Used in African Folk Medicine", 1989.

K. Hishikawa, et al., Japanese Journal of Pharmacology, vol. 85, No. 1, p. 11P, XP-008007448, "Possible Role of a Specific NF-K-B Inhibitor As Anti-Atherosclerosis Agent", Mar. 21-23, 2001.

A. Suzuki, et al., Hypertension Research, vol. 25, No. 1, pp. 99-107, XP-008007437, "Green Coffee Bean Extract and Its Metabolites Have a Hypotensive Effect in Spontaneously Hypertensive Rats", 2002.

U.S. Appl. No. 11/209,672, filed Aug. 24, 2005, Suzuki, et al.
U.S. Appl. No. 11/452,374, filed Jun. 14, 2006, Suzuki, et al.
U.S. Appl. No. 11/813,978, filed Jul. 13, 2007, Ochiai, et al.
Keiko Azuma, et al., "Absorption of Chlorogenic Acid and Caffeic Acid in Rats after Oral Administration", J. Agric. Food Chem., vol. 48, No. 11, 2000, pp. 5496-5500.
U.S. Appl. No. 12/786,910, filed May 25, 2010, Ochiai, et al.

\* cited by examiner

REMEDY FOR HYPERTENSION

CROSS-REFERENCE TO RELATED APPLICATIONS

The present application is a continuation of U.S. Ser. No. 10/810,611, filed on Mar. 29, 2004, which is a continuation of U.S. Ser. No. 10/161,739, filed on Jun. 5, 2002, which claims priority to JP 2001-169261, filed on Jun. 5, 2001.

BACKGROUND OF THE INVENTION

1. Field of the Invention

The present invention relates to a preventive or remedy for hypertension.

2. Description of the Related Art

Cardiac diseases such as angina pectoris, myocardial infarction and heart failure, and cerebrovascular diseases such as cerebral infarction, cerebral hemorrhage and subarachnoid hemorrhage have a close relation to hypertension and they are, respectively, the second and third leading causes of death among Japanese. According to National Livelihood Survey (fiscal 1998) of Health and Welfare Ministry, out of 1000 patients attending a hospital, 64 patients go there for treating hypertension and it is the first leading cause of disease in Japan. For the treatment of hypertension, employed is drug therapy using an antihypertensive such as diuretic, sympatholytic depressant, vasodilator or angiotensin converting enzyme inhibitor. Therapy with such a drug is applied mainly to patients of serious hypertension. General treatment for lifestyle modification including dietetic therapy, therapeutic exercise and cessation of drinking or smoking is, on the other hand, employed for patients at various stages of hypertension from mild hypertension to severe hypertension. Importance of the general treatment has therefore been recognized recently. Of the general treatment, improvement in eating habits is said to be important. There exists a number of foods which have traditionally been said to have an antihypertensive action. In addition, antihypertensive materials derived from foods have been searched extensively, and many active ingredients having an antihypertensive action have been separated or isolated.

Although many of the drugs employed to treat hypertension are satisfactory in their effectiveness, they are not completely free from side effects such as tachycardia and bradycardia and place a heavy burden on patients. Foods which are said to have an antihypertensive action, or active ingredients thereof do not always have satisfactory effectiveness and many of them need enough time to exhibit their antihypertensive effect fully. Recently, the present inventor has found (in Japanese Patent Application No. 2000-107957) that ferulic acid exhibits a high hypertension ameliorating effect while having less side effects. It is however revealed that the antihypertensive effect of ferulic acid does not last long because of its high metabolic rate as measured in vivo.

An object of the present invention is therefore to provide a preventive or remedy for hypertension which has a long lasting antihypertensive effect, has a high degree of safety, does not impose a large stress on patients upon intake of it and has a higher antihypertensive action.

SUMMARY OF THE INVENTION

The present inventor has found that ferulic acid has an antihypertensive action, but owing to a high metabolic rate in vivo, its blood level reaches the maximum about 2 hours after administration and its metabolism and excretion are completed only after about 4 hours, while a specific compound having a ferulic acid skeleton has a long lasting antihypertensive effect because the compound after oral administration is metabolized into ferulic acid and this ferulic acid exists in the blood for a long time. The present inventor has also found that a compound having the specific ferulic acid skeleton is reduced in bitterness peculiar to ferulic acid and therefore has an improved taste, which permits patients to take a sufficient amount daily, and in addition it has a high degree of safety so that it is useful as a preventive or remedy for hypertension.

In one aspect of the present invention, there is thus provided use of a compound represented by the following formula (1) or (2):

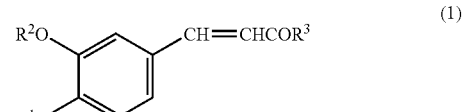

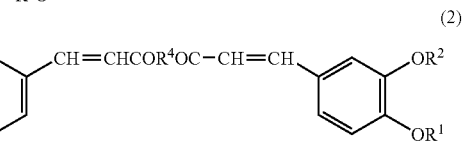

wherein, $R^1$ and $R^2$ are the same or different and each independently represents a hydrogen atom, an alkyl group, an alkenyl group, a cycloalkyl group, a cycloalkenyl group, an alkoxyalkyl group, an aryl group, an alkylaryl group, an aralkyl group or an acyl group, $R^3$ represents a hydroxyl group, an ester bond residue or an amide bond residue, $R^4$ represents an ester bond residue or an amide bond residue, or a pharmaceutically acceptable salt thereof (except ferulic acid) for preparing a preventive or remedy for hypertension.

In another aspect of the present invention, there is also provided a method for treating hypertension, which comprises administering an effective amount of a compound represented by the following formula (1) or (2):

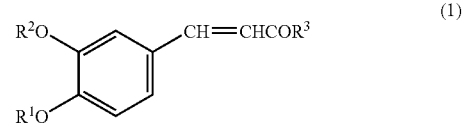

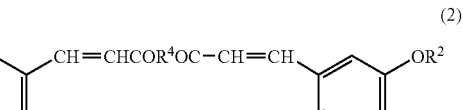

wherein, $R^1$ and $R^2$ are the same or different and each independently represents a hydrogen atom, an alkyl group, an alkenyl group, a cycloalkyl group, a cycloalkenyl group, an alkoxyalkyl group, an aryl group, an alkylaryl group, an aralkyl group, or an acyl group, $R^3$ represents hydroxyl group, an ester bond residue, or an amide bond residue, $R^4$ represents an ester bond residue or an amide bond residue, or a pharmaceutically acceptable salt thereof (except ferulic acid).

When the preventive or remedy for hypertension according to the present invention is administered to patients, ferulic acid stays in their blood for a long period of time, thereby continuously suppressing a blood pressure rise. Moreover, the hypertension preventive or remedy according to the present invention has a reduced bitterness, which bitterness is peculiar to ferulic acid, and this improved taste enables patients to continue medication.

BRIEF DESCRIPTION OF THE INVENTION

Examples of the alkyl, alkenyl, cycloalkyl, cycloalkenyl, alkoxyalkyl, aryl, alkylaryl and aralkyl groups in the formulas (1) and (2) include groups derived from $C_{1-40}$ alcohols or aryl alcohols. Examples of such alcohols or aryl alcohols include linear or branched $C_{1-40}$ alkyl or alkenyl alcohols, aryl alcohols, monoterpene alcohols, sesquiterpene alcohols, diterpene alcohols, triterpene alcohols, sterols, and trimethyl sterols. Specific examples include methanol, ethanol, glycerol, oleyl alcohol, 2-ethylhexyl alcohol, allyl alcohol, cetyl alcohol, menthyl alcohol, phenol, and benzyl alcohol. Of these groups derived from alcohols or aryl alcohols, $C_{1-40}$ alkyl groups such as methyl, ethyl, docosyl and tetradocosyl are preferred from the viewpoint of durability of hypotensive effect, with ethyl, docosyl and tetradocosyl being particularly preferred.

Examples of the acyl group represented by $R^1$ or $R^2$ include acyl groups derived from $C_{1-40}$ carboxylic acids. Such carboxylic acids include $C_{1-40}$ carboxylic acids such as linear or branched alkyl or alkenylcarboxylic acids, arylcarboxylic acids, monoterpenecarboxylic acids, sesquiterpenecarboxylic acids, diterpenecarboxylic acids, triterpenecarboxylic acids and sterolcarboxylic acids. Specific examples include formic acid, acetic acid, lactic acid, citric acid, gluconic acid, fumaric acid, α-ketoglutaric acid, succinic acid, glycolic acid, malic acid, tartaric acid, pyruvic acid, malonic acid, butyric acid, caproic acid, caprylic acid, capric acid, lauric acid myristic acid, palmitic acid, stearic acid, arachidic acid, behenic acid, valeric acid, enanthic acid, pelargonic acid, margaric acid, myristoleic acid, palmitoleic acid, petroselinic acid, oleic acid, vaccenic acid, linolic acid, linolenic acid, eleostearic acid, arachidonic acid, erucic acid, glucuronic acid and mevalonic acid. Of these acyl groups, $C_{1-4}$ alkanoyl groups such as acetyl and formyl, particularly acetyl group, are preferred from the viewpoint of the stability of the resulting compound.

The group $R^3$ is, as well as a hydroxyl group, a residue ester-bonded or amide-bonded to the carboxyl group of a ferulic acid skeleton. The ester-bonded residues include residues derived from linear or branched, monohydric or polyhydric alcohols having 1 to 40 carbon atoms, residues derived from hydroxyl-containing carboxylic acids, and residues derived from sugar alcohol and residues derived from sugar. Monohydric or polyhydric alcohols include alkyl or alkenyl alcohols, aryl alcohols, monoterpene alcohols, sesquiterpene alcohols, diterpene alcohols and triterpene alcohols. Specific examples include monohydric alcohols such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, oleyl alcohol, 2-ethylhexyl alcohol, allyl alcohol, cetyl alcohol, menthyl alcohol, phenol, benzyl alcohol, and diacyl glycerol; and polyhydric alcohols such as glycerol, monoacylglycerol and phosphatidylglycerol.

The hydroxyl-containing carboxylic acids include carboxylic acids containing one hydroxyl group such as citric acid, isocitric acid, malic acid, glycolic acid, cumaric acid, ferulic acid, isoferulic acid, vanillic acid, and homovanillic acid; and carboxylic acid containing two or more hydroxyl groups such as gluconic acid, tartaric acid, quinic acid, Shikimic acid, caffeic acid, gallic acid, vanillylmandelic acid, glucuronic acid and mevalonic acid.

Of these hydroxyl-containing carboxylic acids, quinic acid, Shikimic acid, cinnamic acid, cumaric acid, citric acid, caffeic acid, ferulic acid, dimethoxycinnamic acid, gallic acid, and glucuronic acid are preferred from the viewpoint of durability of an antihypertensive effect, with quinic acid being especially preferred.

Sugar alcohols include natural sugar alcohols, especially those contained in plants, sugar alcohols obtained by subjecting plants to chemical treatment upon extraction and/or fractionation, and sugar alcohols obtained by chemical modification of natural ones. Specific examples include alcohols obtained by the reduction of the carbonyl group of a monosaccharide, oligosaccharide or polysaccharide. Monosaccharide alcohols include erythritol which is a four-carbon sugar alcohol obtained by fermentation and decomposition of D-glucose with a yeast, xylitol which is a five-carbon sugar, sorbitol which is a six-carbon sugar, and mannitol. Specific examples of oligosaccharide include palatinit (hydrogenated palatinose), maltitol (hydrogenated maltose), lactitol and branched oligosaccharide alcohol. Polysaccharide alcohols include hydrogenated dextrin used as a glutinous starch syrup.

Of these sugar alcohols, erythritol, xylitol, sorbitol, and mannitol are preferred, with erythritol being especially preferred.

Saccharides include arabinose, galactose, glucose, fructose, mannose, ribose, maltose, cellobiose, sucrose and lactose and polymers thereof. Of these, arabinose and galactose, and polymers thereof are especially preferred.

The amide-bonded residues as $R^3$ include residues derived from water soluble amino acids. Examples of such an amino acid include glycine, alanine, valine, leucine, isoleucine, phenylalanine, proline, serine, threonine, cysteine, cystine, methionine, tryptophan, tyrosine, asparagine, glutamine, aspartic acid, glutamic acid, lysine, arginine and histidine. Of these amino acids, glycine and tyrosine are preferred from the viewpoint of durability of antihypertensive effect, with glycine being especially preferred.

Of the groups $R_3$, residues derived from $C_{1-40}$ alcohols such as ethanol, docosanol and tetracosanol; residues derived from hydroxyl-containing carboxylic acids such as quinic acid, gallic acid, citric acid and glucuronic acid, and amino acid residues such as glycine are preferred from the viewpoint of the durability of antihypertensive effect.

The group $R^4$ represents any one of ester-bonded residues and amide-bonded residues, of which preferred are ester-bonded residues such as residues derived from polyhydric alcohols such as glycerol, monoacyl glycerol and phosphatidylglycerol; residues derived from carboxylic acid having at least 2 hydroxyl groups such as gluconic acid, tartaric acid, quinic acid, Shikimic acid, caffeic acid, gallic acid, vanillylmandelic acid, glucuronic acid, and mevalonic acid; and residues derived from sugar alcohols or saccharides. When the group $R^4$ is a residue derived from sugar alcohols or saccharides, the sugar alcohols or saccharides described above as $R^3$ are usable as $R^4$.

As the group $R^4$, residues of arabinose, gallic acid, quinic acid and glucuronic acid are especially preferred from the viewpoint of durability of an antihypertensive effect.

As the compounds represented by the formula (1) or (2), preferred are chlorogenic acids. Specific examples include 3-caffeoylquinic acid (neochlorogenic acid), 4-caffeoylquinic acid (cryptochlorogenic acid), 5-caffeoylquinic acid (chlorogenic acid), 3,4-dicaffeoyl quinic acid, 3,5-dicaffeoil quinic acid, 4,5-dicaffeoyl quinic acid, 3-feruloylquinic acid, 4-feruloylquinic acid, 5-feruloylquinic acid, and 3-feruloyl-4-caffeoylquinic acid.

Examples of the extract from plants other than chlorogenic acids include dimethyl caffeate ether, phenylethyl caffeate, 2-O-caffeoyl-albutin, caffeoyl-calleryanin, 3-O-caffeoyl-shikimic acid, fukinolic acid, echinacoside, 1,3-dicaffeoylquinic acid, cichoric acid, coniferyl alcohol, curcumin, lignan and lignine.

Of these natural substances, 3-caffeoylquinic acid (neochlorogenic acid), 4-caffeoylquinic acid (cryptochlorogenic acid), 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, 3-feruloyl-4-caffeoylquinic acid, 1,3-dicaffeoylquinic acid, lignan, and curcumin are preferred from the viewpoint of durability of an antihypertensive effect, with 3-caffeoylquinic acid, 4-caffeoylquinic acid, 5-caffeoylquinic acid and curcumin are especially preferred.

Of the compounds represented by the formula (1) or (2), especially preferred compounds include caffeoyl glucuronide, caffeoylglycine, feruloylglycine, feruloyl-arabinose, 3-feruloyl-4-caffeoyl arabinose, 3-caffeoylquinic acid, 4-caffeoylquinic acid and 5-caffeoylquinic acid.

The compounds of the formula (1) or (2) to be used in the invention can be extracted from natural substances, particularly plants, containing them, while they can be prepared industrially by chemical synthesis.

In the latter case, the compounds can be prepared by reacting ferulic acid with an alcohol, carboxylic acid and the like corresponding to $R^1$, $R^2$, $R^3$ and $R^4$. Ferulic acid used as the raw material can be obtained by hydrolysis of a ferulate ester, which is available from plants, with hot sulfuric acid under pressure, followed by purification; or by culturing bacteria (*Pseudomonas*) in a broth containing a clove oil obtained by steam distillation of buds and leaves of *Syzygium aromaticum* MERRILL et PERRY or a broth containing eugenol available by purification of the clove oil, followed by separation of the resulting culture broth and purification. When ferulic acid is prepared by chemical synthesis, condensation reaction of vanillin with malonic acid can be employed (Journal of American Chemical Society, 74, 5346(1952)). Ferulic acid has stereoisomers. Any one of them is usable. A mixture of the isomers is also usable.

Preferred examples of the plants from which the ferulate ester, among the compounds represented by the formula (1) or (2), is extracted include coffee, apple, grape, onion, Japanese radish, lemon, *Cnidium officinale, Angelicae radix,* turpentine tree, *Coptis Rhizome,* turmeric, *Ferula assafoetida* L., sweet potato, leaves of sunflower, seeds of sunflower, jew's mallow sugarcane, corn, wheat, barley and rice, with rice being particularly preferred. The term "rice" as used herein means raw or dry seeds of rice (*Oryza sativa* LINNE).

The compounds represented by the formula (1) or (2) include those prepared by chemical treatment of the extract or fraction, which has been obtained from a natural substance, particularly, a plant; and those prepared by chemical modification of the natural substance. For example, a rice bran oil obtained from rice bran is separated using hydrous ethanol and hexane and then ethyl ferulate is available from the hydrous ethanol fraction.

The compounds represented by the formula (1) or (2) are available by direct extraction from natural substances. In this case, they are prepared as a mixture of an ester compound, amide compound and ether compound. Extraction from plants such as raw coffee beans, leaves of a nandina and unripe apple fruits yields a mixture of chlorogenic acids. Alternatively, extraction of the seeds of *Coffea arabica* LINNE with a warm aqueous solution of ascorbic acid or citric acid produces chlorogenic acids to which ascorbate or citrate ester has been ester-bonded.

The compounds represented by the formula (1) or (2) have improved water solubility and enhanced physiological availability when they are in the form of a pharmaceutically acceptable salt. No particular limitation is imposed on the salt of ferulic acid insofar as it is pharmaceutically acceptable. Examples of a basic substance for the formation of such a salt include hydroxides of an alkali metal such as lithium hydroxide, sodium hydroxide and potassium hydroxide, hydroxides of an alkaline earth metal such as magnesium hydroxide and calcium hydroxide, inorganic bases such as ammonium hydroxide and basic amino acids such as arginine, lysine, histidine and ornithine, and organic bases such as monoethanolamine, diethanolamine and triethanolamine. Of them, hydroxides of an alkali metal or alkaline earth metal are particularly preferred.

The hypertension preventive or remedy according to the present invention may be prepared by first preparing a salt of the above-described compound and adding the salt into a composition made of other components, or by adding ferulic acid and a salt-forming component therewith to the composition separately, thereby forming the salt in the resulting mixture.

The hypertension preventive or remedy according to the present invention is preferably administered to an adult (weight: 60 kg) in an amount of about 0.001 to 50 g, preferably about 0.003 to 20 g, especially about 0.05 to 10 g a day in terms of ferulic acid. When a plant extract is employed, the amount in terms of dry weight can be administered.

The hypertension preventive or remedy according to the present invention can be prepared as an orally administrable or parenterally administrable composition by adding to its effective ingredient a pharmaceutically acceptable carrier. Of them, the orally administrable composition is preferred. Examples of the orally administrable composition include tablets, granules, fine subtilaes, pills, powders, capsules (including hard capsules and soft capsules), troches, chewables and liquids (medical drinks).

The hypertension preventive or remedy according to the present invention has a high degree of safety so that no problem occurs even if those who have a normal blood pressure usually take it as a food or beverage. The preventive or remedy of the present invention can be taken as a beverage such as juice or coffee, a liquid food such as soup, an emulsion or pasty food such as milk or curry, a semi-solid food such as jelly and gummy, a solid food such as gum, tofu or supplement, a powdery food, or an oil- or fat-containing food such as margarine, mayonnaise or dressing.

The compound of the present invention is added to such a beverage or drink in an amount of 0.001 to 50 wt. %, preferably 0.01 to 25 wt. %, especially 0.1 to 10 wt. %. The content of ferulic acid is confirmed by high-performance liquid chromatography equipped with an electrochemical detector.

EXAMPLES

Example 1

Identification of an Antihypertensive Component

1) Animals Provided for Test

Each of 15 week-old, spontaneously hypertensive male rats ("SHR") was anesthetized and its blood pressure was measured at the carotid artery by using a commercially available noninvasive sphygmomanometer for rats (manufactured by Softlon Co., Ltd.). Its electrocardiograph was recorded by an electrocardiogram. A sample was injected to the femoral vein through a catheter. After the rats were accustomed sufficiently to the sphygmomanometric operation, the evaluation test was started. The rats were all bred under conditions (in a breeding room in a rat region) at a room temperature of 25±1° C., humidity of 55±10% RH and illumination for 12 hours (from 7:00 am to 7:00 pm).

(2) Administration Method and Amount

In the control plot, physiological saline was employed. In Test plot 1, Test plot 2 and Test plot 3, a solution of 5 μg mol/kg caffeic acid in physiological saline, a solution of 5 μg mol/kg quinic acid in physiological saline and a solution of 5 μg mol/kg ferulic acid in physiological saline were used, respectively.

(3) Test Method

Through a catheter, the sample was intravenously administered and while administration, systolic blood pressures of the carotid artery were measured with the passage of time.

Fluctuations in the blood pressure was not recognized when caffeic acid or quinic acid was intravenously administered, while lowering in the blood pressure was recognized when ferulic acid was administered.

Example 2

Measurement of an Antihypertensive Effect

1) Animals Provided for Test

After each of 15 week-old, spontaneously hypertensive male rats ("SHR") was accustomed to sphygmomanometric operation by preliminarily measuring its blood pressure for 7 successive days using a commercially available noninvasive sphygmomanometer for rats (manufactured by Softlon Co., Ltd.), the evaluation test was started. The rats were all bred under conditions (in a breeding room in a rat region) at a room temperature of 25±1° C., humidity of 55±10% RH and illumination for 12 hours (from 7:00 am to 7:00 pm).

(2) Administration Method and Amount

In the test plot (Comparative Example), a solution of ferulic acid (50 mg/kg as a dose) in physiological saline was employed. In Test plot 2, Test plot 3, Test plot 4, Test plot 5 and Test plot 6, a solution of chlorogenic acid (50 mg/kg as a dosage) in physiological saline, oryzanol (50 mg/kg as a dosage), curcumin (50 mg/kg as a dosage), phenylethyl caffeate (50 mg/kg as a dosage) and rosmarinic acid (50 mg/kg as a dosage) were used, respectively. In each test plot, physiological saline was employed as a control. Each of the samples was orally administered.

(3) Test Method

SHRs were fasted overnight and divided into groups, each consisting of 5 rats. Systolic blood pressures of the caudal artery were measured prior to administration, and several times during 30 minutes to 24 hours after administration (4) Statistical Treatment Method The test results thus obtained were expressed by the mean value (%) and standard deviation (SE) of the changing ratio (%) in systolic blood pressure.

A lowering ratio of the systolic blood pressure measured during 30 minutes to 24 hours each after administration relative to the systolic blood pressure prior to administration is shown in Table 1.

TABLE 1

Successive blood pressures after the administration of various test samples

| | | Time | | | | | | | | | |
|---|---|---|---|---|---|---|---|---|---|---|---|
| | | 0 | 0.5 | 1 | 2 | 3 | 4 | 6 | 9 | 12 | 24 |
| Control | Mean | 0 | −0.5 | −0.3 | −2.1 | | 0.2 | −0.5 | | | |
| | S.E | 0 | 2.4 | 1.1 | 1.9 | | 1.4 | 1.5 | | | |
| Test plot 1 | Mean | 0 | −9.5 | −10.3 | −6.8 | | −7.9 | −3.2 | | | |
| | S.E | 0 | 1.5 | 1.1 | 1.4 | | 1 | 1.7 | | | |
| Control | Mean | 0 | | | | −0.2 | | −1.3 | −2.4 | −2.2 | −1.4 |
| | S.E | 0 | | | | 1.5 | | 1 | 1 | 1.1 | 1.8 |
| Test plot 2 | Mean | 0 | | | | −4 | | −6.7 | −7.3 | −6.8 | −2.9 |
| | S.E | 0 | | | | 1.7 | | 1.8 | 3.9 | 2.3 | 2.8 |
| Control | Mean | 0 | | | | | | 0.3 | | −0.5 | 5.6 |
| | S.E | 0 | | | | | | 2.9 | | 2.1 | 6.9 |
| Test plot 3 | Mean | 0 | | | | | | −8.5 | | −9.1 | −11.0 |
| | S.E | 0 | | | | | | 1.8 | | 3.8 | 2.0 |
| Test plot 4 | Mean | 0 | | | | | | −11.1 | | −9.0 | −11.2 |
| | S.E | 0 | | | | | | 1.8 | | 0.0 | 4.5 |
| Test plot 5 | Mean | 0 | | | | | | −15.2 | | −3.5 | −5.3 |
| | S.E | 0 | | | | | | 1.4 | | 4.5 | 5.3 |
| Test plot 6 | Mean | 0 | | | | | | −13.7 | | −1.3 | −0.7 |
| | S.E | 0 | | | | | | 1.4 | | 0.3 | 1.6 |
| Test plot 7 | Mean | 0 | | | | | | −6.4 | | 0.9 | 2.2 |
| | S.E | 0 | | | | | | 6.6 | | 1.4 | 1.6 |
| Control | Mean | 0 | | −0.5 | −2.2 | | −4.2 | | | | |
| | S.E | 0 | | 0 | 0 | | 0 | | | | |
| Test plot 8 | Mean | 0 | | −15.2 | −12.8 | | −13.8 | | | | |
| | S.E | 0 | | 0 | 0 | | 0 | | | | |

* Test plot 1 (ferulic acid 50 mg/Kg)
Test plot 2 (5-chlorogenic acid 50 mg/Kg)
Test plot 3 (4-chlorogenic acid 50 mg/Kg)
Test plot 4 (3-chlorogenic acid 50 mg/Kg)
Test plot 5 (curcumin 50 mg/Kg)
Test plot 6 (phenylethyl caffeic acid 50 mg/Kg)
Test plot 7 (rosemaric acid 50 mg/Kg)
Test plot 8 (oryzanol 50 mg/Kg)

As is apparent from Table 1, rats in Test plots 2 to 6 each exhibited a long-lasting antihypertensive effect compared with those in Test plot 1 (ferulic acid).

Example 3

Measurement the Blood Level of Ferulic Acid (1) Animals Provided for the Test

Each of 15 week-old, spontaneously hypertensive male rats ("SHR") was preliminarily bred in a similar manner to Example 2.

(2) Administration Method and Amount

To the SHR, 200 mg/kg of chlorogenic acid was orally administered once.

(3) Test Method

SHRs were fasted overnight and then divided into groups, each consisting of 5 rats. The blood levels of chlorogenic acid, caffeic acid and ferulic acid were measured prior to administration and several times during from 30 minutes to 24 hours, each after administration.

The blood levels of chlorogenic acid, caffeic acid and ferulic acid measured prior to administration and several times during from 30 minutes to 24 hours, each after administration are shown in Table 2.

TABLE 2

Successive blood levels of chlorogenic acid, caffeic acid and ferulic acid after the administration of chlorogenic acid

| | Time | | | | | |
|---|---|---|---|---|---|---|
| | 0 | 3 | 6 | 9 | 12 | 24 |
| Chlorogenic acid | 0 | 0 | 0 | 0 | 0 | 0 |
| Caffeic acid | 0 | 0.07 | 0.179 | 0.166 | 0.05 | 0 |
| Ferulic acid | 0 | 0.074 | 0.154 | 0.174 | 0.145 | 0 |

As is apparent from Table 2, not chlorogenic acid but caffeic acid and ferulic acid were observed in the blood, indicating that chlorogenic acid was metabolized into caffeic acid and ferulic acid promptly after oral administration. The time-dependent change has revealed the occurrence of in vivo conversion from caffeic acid into ferulic acid.

Example 4

Measurement of the Blood Level of Ferulic Acid (1) Test Subject, Administration Method and Administration Amount A beverage mixture containing an extract of raw coffee beans (chlorogenic acid group: 280 mg/day in terms of the amount of chlorogenic acid) was fed to 5 healthy subjects for successive 6 weeks. From the patients who did not take breakfast, the blood was collected 24 hours after final drinking. The blood was also collected under similar conditions from the group (placebo group: 0 mg/kg of chlorogenic acid administered, the group consisting of 3 subjects) free from the successive application of the above-described beverage mixture containing an extract from raw coffee beans.

(3) Test Method

The blood levels of chlorogenic acid, caffeic acid and ferulic acid were measured using liquid chromatography.

TABLE 3

Blood levels of caffeic acid and ferulic acid 24 hours after administration of chlorogenic acid (280 mg/Kg in terms of human body weight)

| | Placebo group | (µg/mL plasma) Chlorogenic acid group |
|---|---|---|
| Caffeic acid | 0.009 | 0.0954 |
| Ferulic acid | 0 | 0.1044 |

The results are as shown in Table 3. In the blood, not chlorogenic acid but caffeic acid and ferulic acid were observed, suggesting that even in oral administration to human being, chlorogenic acid was metabolized into caffeic acid and ferulic acid. The time-dependent change has revealed the occurrence of in vivo conversion of caffeic acid to ferulic acid.

From Examples 1 to 4, it has been understood that exhibition of the antihypertensive effect of chlorogenic acid, quinic acid or caffeic acid owes to the metabolism of them into ferulic acid, but chlorogenic acid, quinic acid or caffeic acid has a markedly long-lasting antihypertensive effect so that it is useful as an antihypertensive.

Example 5

Soft Capsules

| Gelatin | 70.0 (wt. %) |
|---|---|
| Glycerin | 22.9 |
| Methyl paraoxybenzoate | 0.15 |
| Methyl paraoxybenzoate | 0.15 |
| Propyl paraoxybenzoate | 0.51 |
| Water | 6.44 |

Soft capsules (oval-type, weight: 150 mg) composed of the above-described composition were filled with 400 mg of soybean oil, 50 mg of dicaffeoyl tartaric acid and 50 mg of eicosanol caffeate in a manner known per se in the art. These capsules exhibited a good antihypertensive action when orally administered.

Example 6

The using example as a beverage will next be described.

| Skim milk | 3.5 (wt. %) |
|---|---|
| Enzyme-hydrolyzed milk casein | 3.5 |
| Fructose | 9.0 |
| Eicosylferulate ester | 0.1 |
| 3-Feruloyl-4-Caffeoylarabinose | 10.0 |
| Citric acid | 0.1 |
| Ascorbic acid | 0.1 |
| Flavor | 0.1 |
| Water | 73.6 |

It has been found that the beverage made of the above-described composition had high storage stability and had good taste.

Example 7

An application example to wheat flour products will next be described.

| | |
|---|---|
| Rapeseed oil | 15 (g) |
| Corn starch | 15 |
| Wheat flour | 42.6 |
| Butter | 5 |
| Fructose | 14 |
| Caffeoylglycine | 2 |
| Ferulyl-citric acid | 0.4 |
| Table salt | 0.5 |
| Sodium bicarbonate | 0.5 |
| Water | 5 |

Cookies made of the above-described composition were baked.

What is claimed is:

1. A method for treating hypertension, which comprises administering to a patient in need thereof an effective amount of a composition comprising a compound selected from the group consisting of at least one of 4-caffeoylquinic acid and chlorogenic acid, or a pharmaceutically acceptable salt thereof, wherein the compound or pharmaceutically acceptable salt thereof is the only component in said composition which is active against hypertension.

2. The method of claim 1, wherein the compound is 4-caffeoylquinic acid, or a pharmaceutically acceptable salt thereof.

3. The method of claim 1, wherein the compound is chlorogenic acid, or a pharmaceutically acceptable salt thereof.

4. The method of claim 1, wherein said effective amount ranges from 0.001 to 50 g.

5. The method of claim 1, wherein said composition further comprises a pharmaceutically acceptable carrier.

6. The method of claim 1, wherein said administering is orally.

7. The method of claim 6, wherein said composition is in a form selected from the group consisting of tablets, granules, fine subtilaes, pills, powders, hard capsules, soft capsules, troches, chewables and liquids.

8. The method of claim 6, wherein said composition is in a liquid form.

9. The method of claim 8, wherein said compound is in an amount of 0.001 to 50wt.%.

10. The method of claim 1, wherein said administering is parenterally.

11. A method for treating hypertension, which comprises administering to a patient in need thereof an effective amount of a composition comprising phenethyl caffeate, or a pharmaceutically acceptable salt thereof.

12. The method of claim 11, wherein said effective amount ranges from 0.001 to 50 g.

13. The method of claim 11, wherein said composition further comprises a pharmaceutically acceptable carrier.

14. The method of claim 11, wherein said administering is orally.

15. The method of claim 14, wherein said composition is in a form selected from the group consisting of tablets, granules, fine subtilaes, pills, powders, hard capsules, soft capsules, troches, chewables and liquids.

16. The method of claim 14, wherein said composition is in a liquid form.

17. The method of claim 16, wherein said compound is in an amount of 0.001 to 50wt.%.

18. The method of claim 11, wherein said administering is parenterally.

* * * * *